United States Patent [19]

Kato et al.

[11] Patent Number: 4,677,374
[45] Date of Patent: Jun. 30, 1987

[54] OIL MIST DECTECTOR

[75] Inventors: Takayuki Kato, Aichi; Makoto Miyamoto, Kariya, both of Japan

[73] Assignee: Aisin Seiki Kabushiki Kaisha, Kariya, Japan

[21] Appl. No.: 795,100

[22] Filed: Nov. 5, 1985

[30] Foreign Application Priority Data

Nov. 5, 1984 [JP] Japan ............................. 59-233851

[51] Int. Cl.$^4$ ........................................ G01R 27/02
[52] U.S. Cl. .................................... 324/65 R; 73/116
[58] Field of Search .............. 73/116; 324/65 R, 65 P

[56] References Cited

U.S. PATENT DOCUMENTS

| | | | |
|---|---|---|---|
| 2,930,015 | 3/1960 | Blumer | 324/65 R |
| 2,994,821 | 8/1961 | Dravnieks | 324/65 R |
| 3,731,187 | 5/1973 | Hausler et al. | 324/65 R |
| 4,080,564 | 3/1978 | Nitta et al. | 324/65 R |
| 4,475,382 | 10/1984 | Frank | 73/116 |

FOREIGN PATENT DOCUMENTS

| 079876 | 8/1971 | Japan | 324/65 R |
|---|---|---|---|
| 0124515 | 7/1983 | Japan | 324/65 R |

*Primary Examiner*—Stewart J. Levy
*Assistant Examiner*—Robert R. Raevis
*Attorney, Agent, or Firm*—Oblon, Fisher, Spivak, McClelland & Maier

[57] ABSTRACT

An oil mist detector comprising a heating unit capable of attaching oil mist in non-inflammable gas to itself to deposit the oil mist attached to itself by the exothermic reaction, a detecting means for detecting an amount of current leaking through the deposit to heat the heating unit and an indicating means for indicating the current detected by the detecting means as an amount of the oil mist.

2 Claims, 5 Drawing Figures

OIL MIST DECTECTOR

FIELD OF THE INVENTION

This invention relates to an oil mist detector in which oil mist in non-inflammable gas is decomposed and deposited on a heating unit by heat decomposition and an amount of current leaking to heat said heating unit through the corresponding deposit is detected so that an amount of the oil mist is detected from the leak current through the corresponding deposit.

BACKGROUND OF THE INVENTION

Recently, in an enclosed reciprocating engine for a sterling engine, a seal portion to seal a cylinder having a piston fitted therein against a guide rod for transmitting the reciprocating motion of the piston to the outside of the cylinder is provided and sometimes uses oil. Thus, the oil leaking from the seal portion produces oil mist to pollute the interior of the cylinder, and a problem was presented that it interferes with the reciprocating motion of the piston. Hence, the oil mist in the cylinder needs to be measured during the reciprocating motion of the piston.

In conventional measuring apparatus, for example, a piezo-balance dust meter, a piezoelectric element was used for an oil mist measuring sensor. Thus it cannot be disposed in the cylinder having pressure fluctuates so as to measure directly the oil mist. That is, it samples gas in the cylinder to measure indirectly oil mist in a space separate from the cylinder after pressure is rendered constant. Thus, since accuracy in measurement was not obtained and further a sampling piping was needed, the measuring apparatus inevitably the defect of being large-scaled.

Hereinafter will be described an embodiment according to the prior art with reference to the drawings.

FIG. 5 shows a sterling engine 10 for converting energy of high temperature and pressure gas into a turning force.

Cylinders 11 including ones not shown are provided symmetrically at four positions. A piston 12 disposed in each cylinder 11 is formed on both ends with an expansion chamber 13 and a compression chamber 14. Each expansion chamber 13 and compression chamber 14 communicate respectively to heat exchangers 15a, 15b of supply sources of working gas.

In each piston 12 is disposed a guide rod 16 which transmits the reciprocating motion of the piston 12 to the outside of the cylinder 11 through a rod seal 17 system. To the guide rod 16 is connected a guide piston 18 which is slidably disposed in a guide cylinder 19. Each guide piston 18 engages a swash plate 20 which has a rotary shaft 21.

The engine 10 thus constituted is supplied with high temperature and pressure helium gas sequentially through the heat exchangers 15a, 15b and each piston 12 reciprocates cyclically in the cylinder 11.

This reciprocating motion is transmitted through the guide rod 16 and the respective guide pistons 18 reciprocate with a certain phase difference therebetween. Thus, the swash plate 20 engaging each guide piston 18 will rotate and the rotation is transmitted to the outside through the rotary shaft 21.

Here, will be described the constitution of the rod seal system 17 for maintaining the cylinder 11 air-tight against the guide rod 16 with respect to FIG. 5.

The rod seal system 17 is constituted such that around the guide rod 16 from the compressor chamber 14 side are sequentially disposed a gas seal 26, an intermediate chamber 25 communicating to the compression chamber 14, an oil scraper 22, a liquid enclosing chamber 23 and an oil seal 24, and the liquid enclosing chamber 23 communicates to the upper portion of the oil scraper 22 through an oil tank 27.

Thus, since oil is used for sealing, oil disposed in the liquid enclosing chamber 23 has a possibility of leaking to the compression chamber 14 through the oil scraper 22, intermediate chamber 25 and gas seal 26. Hence, in the compression chamber 14 of the engine 10 will be distributed oil in the form of mist.

This oil mist deposits on the inside wall of a pipe of the heat exchanger through a pipe interconnecting the heat exchanger and the compression chamber 14.

As the deposit of this oil mist on the inside wall of the pipe is accumulated, gas flow path in the pipe will be blocked to degrade the efficiency of heat exchange of helium gas while degrading the efficiency of engine itself.

Also, when the efficiency of the filter 28 is degraded, the oil mist will be similarly in the form of mist distributed in the compression chamber 14 through the oil scraper 22, intermediate chamber 25 and filter 28.

Thus, the detection of oil mist concentration in the compression chamber 14 of the engine 10 is an important subject for maintaining the performance of the compressor.

SUMMARY OF THE INVENTION

Accordingly, an object of this invention is to overcome said defects in measuring an oil mist amount by depositing and decomposing the mist on the high temperature surface of a heater in the corresponding mist atmosphere and using a small-sized sensor means for detecting the oil mist amount as a change in current leaking through the deposit so that the oil mist amount in a cylinder can be directly measured.

This invention provides an oil mist detector in which a heating unit capable of attaching oil mist in non-inflammable gas is disposed to deposit the oil mist attached to the heating unit by the heat decomposition of the heating unit, and an amount of current leaking to heat the heating unit through the deposit is detected to detect the oil mist amount from the leak current through the corresponding deposit.

According to said invention, the concentration of oil mist can be extremely easily measured by the change in leak current on the surface of a compact heater in the oil mist within a cylinder.

Thus, this oil mist detector can very effectively and directly measure the oil mist amount in the cylinder without being affected by pressure fluctuation in the cylinder and further, compared with the case in which gas in the cylinder is sampled to measure the oil mist amount, can very easily and accurately grasp measure the oil mist concentration. When the oil mist detector according to this invention is attached to portion Ⓐ in the compression chamber 14 of the engine 10 or portion Ⓑ between the filter 28 and the compression chamber 14, the concentration of oil mist can always be monitored.

Consequently, defective oil scrapers and gas seals, and the degradation of the efficiency of filters, etc. can be found.

Further, as compared with the structure of the inventors' copending U.S. patent application Ser. No. 795,180 for detecting deposit as a resistance value, since this oil mist detector detects the leak current from the deposit of oil mist attached to the surface of a heater, it does not need any separate connections for the electrode means and heater from the power supply means so that the sensor means itself and detector itself can be simplified and very easily and effectively put to practical use.

DETAILED DESCRIPTION OF THE INVENTION

Figure 5:
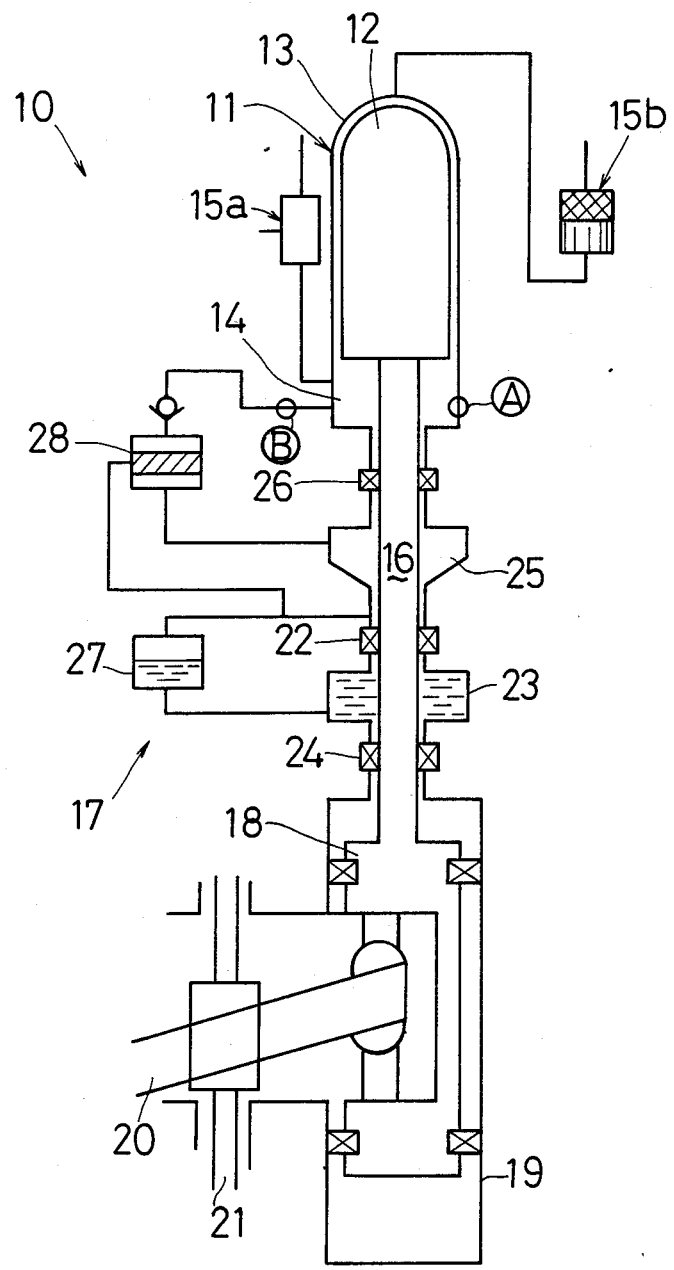
FIG. 5 is a drawing showing an engine for which an oil mist is measured.

Hereinafter will be described a preferable embodiment of an oil mist sensor attachable to portions Ⓐ, Ⓑ of a compressor shown in FIG. 5 with reference to the drawings.

The compression chamber of the engine is filled with helium gas and a cylinder is driven by the compression of the helium gas.

Thus, since oxygen is not present in the compression chamber, oil mist does not burn. It is the fundamental principle of the oil mist detector according to this invention that by utilizing this atmosphere the oil mist is deposited and decomposed on the high temperature surface of a heater without burning the oil mist and current leaking through the corresponding deposit is measured to detect the oil mist amount.

Figure 2:
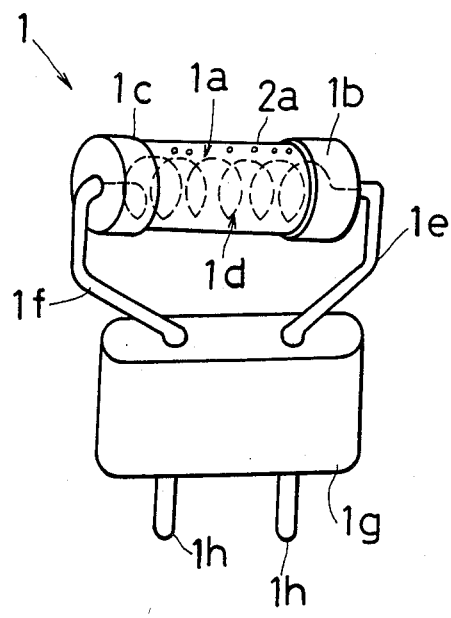
FIG. 2 is a perspective view showing a first embodiment of an oil mist detector according to this invention.

With respect to FIG. 2 will be detailed the oil mist detector according to this invention.

Figure 1:
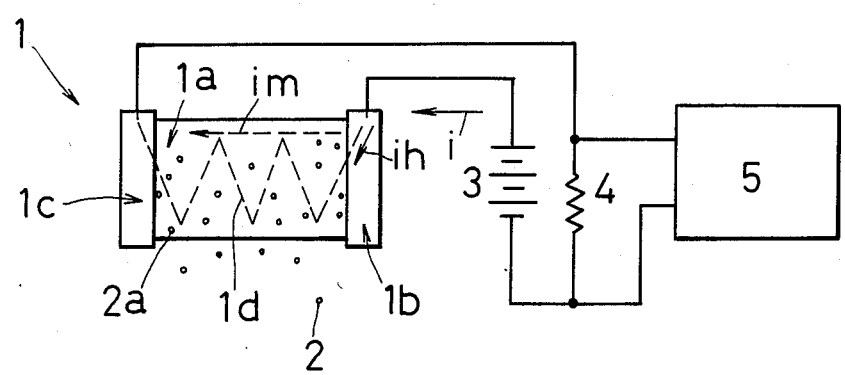
FIG. 1 is a schematic illustration showing the principle of operation of an oil mist sensor according to this invention.

In FIG. 1, when oil mist 2 is attached to the surface of a mist sensor 1 heated to high temperature, the oil mist is decomposed on the surface of the sensor 1 as a detector to provide deposit 2a having carbon as a main component.

The mist sensor 1 is heated to high temperature by a power source 3 through a heating wire 1d in the sensor to maintain at about 850° C. the surface of a coating 1a having excellent heat resisting property and insulating property like ceramic coating the heating wire 1d. As under this condition said oil mist 2 is deposited on the surface of the coating 1a and decomposed, and a great amount of this deposit 2a is accumulated on the surface of the coating 1a, current im leaking from terminal portions 1b and 1c via the deposit 2a other than heating current ih flows due to the conductivity of the deposit 2a, and current i=ih+im will flow from said power source 3. This current is detected by a load resistance 4 and the oil mist amount is indicated by an indicating means 5.

Thus, the wider the contact area of terminal portions 1b, 1c of the heating wire 1d and the deposit 2a is, the greater the sensitivity of measurement of the leak current im to the deposit 2a accumulated on the surface of the coating 1a.

In the oil mist sensor according to this invention, preferable sensor surface temperature for depositing oil mist in helium gas is about 750°–900° C. This is a necessary temperature for depositing carbon included in the oil mist.

However, the black deposit (carbon) of the oil mist accumulated on the surface of the sensor includes, in addition to the carbon, sulfur, phosphorus and various additives included in oil itself. Since the amount of these components is very small, the deposit 2a on the surface of sensor mainly consists of the a sintered carbide having electric conductivity. Thus, as shown in FIG. 1, the leak current im between the terminal portions 1b, 1c of the sensor 1 increases gradually from zero value as the deposit 2a builds up and further the degree of the increase is varied with the concentration of the mist due to decreased resistance for im with increased sectional area of the deposit.

Next will be described a particular embodiment of the mist sensor 1 as a detector according to this invention with reference to FIG. 2. The heating wire 1d such as nichrome wire and kanthal wire is wound around the mist sensor 1. The coating 1a such as ceramic is sintered on the heating wire 1d and the terminal portions 1b, 1c are provided on both ends of the coating 1a. The heating wire 1d and terminal portion 1b, 1c are constructed to be connected to terminals 1e, 1f of socket 1g made of material having excellent insulating property and heat resisting property and to the external circuit through pin terminals 1h respectively. By such construction, the heating wire 1d becomes exothermic when current is supplied from the outside power source 3 and the surface temperature of the coating 1a is heated up to 750°–900° C. When oil mist exists in the helium gas atmosphere within the compression chamber of the compressor under the heated condition, the mist is decomposed to sintered carbide on the coating 1a to provide the deposit.

When this deposit 2a is accumulated, the surface of the coating 1a having insulating property becomes conductive so that heating current to supply current to the heating wire 1d will leak at the surface of the coating 1a through the corresponding deposit 2a.

When the heating current for the heating wire 1d is designated by ih as shown in FIG. 1, since the heating current ih is constant irrespective of the presence of the deposit 2a, current i=ih+im flows from the power source 3 with the leak current im flowing to the surface of the coating 1a. Thus, when the leak current im is detected by the load resistance 4 and the indicating means 5, a deposit amount, i.e., oil mist amount on the deposit 2a due to the oil mist 2 on the coating 1a can be detected.

The amount of oil mist baked on the surface of the coating 1a of the sensor 1 represents an integrated value since it is accumulated according to time and the concentration of mist.

Then, when the relationship between the concentration of mist, time and the leak current is beforehand examined, the oil mist amount can be detected from the value of the leak current im of the sensor 1, and whether or not the oil mist amount is less than a specified one can be found by setting a judging criterion value to the corresponding leak current im. That is, a leak current im can be compared to a known leak current for a known oil mist concentration.

Figure 3:
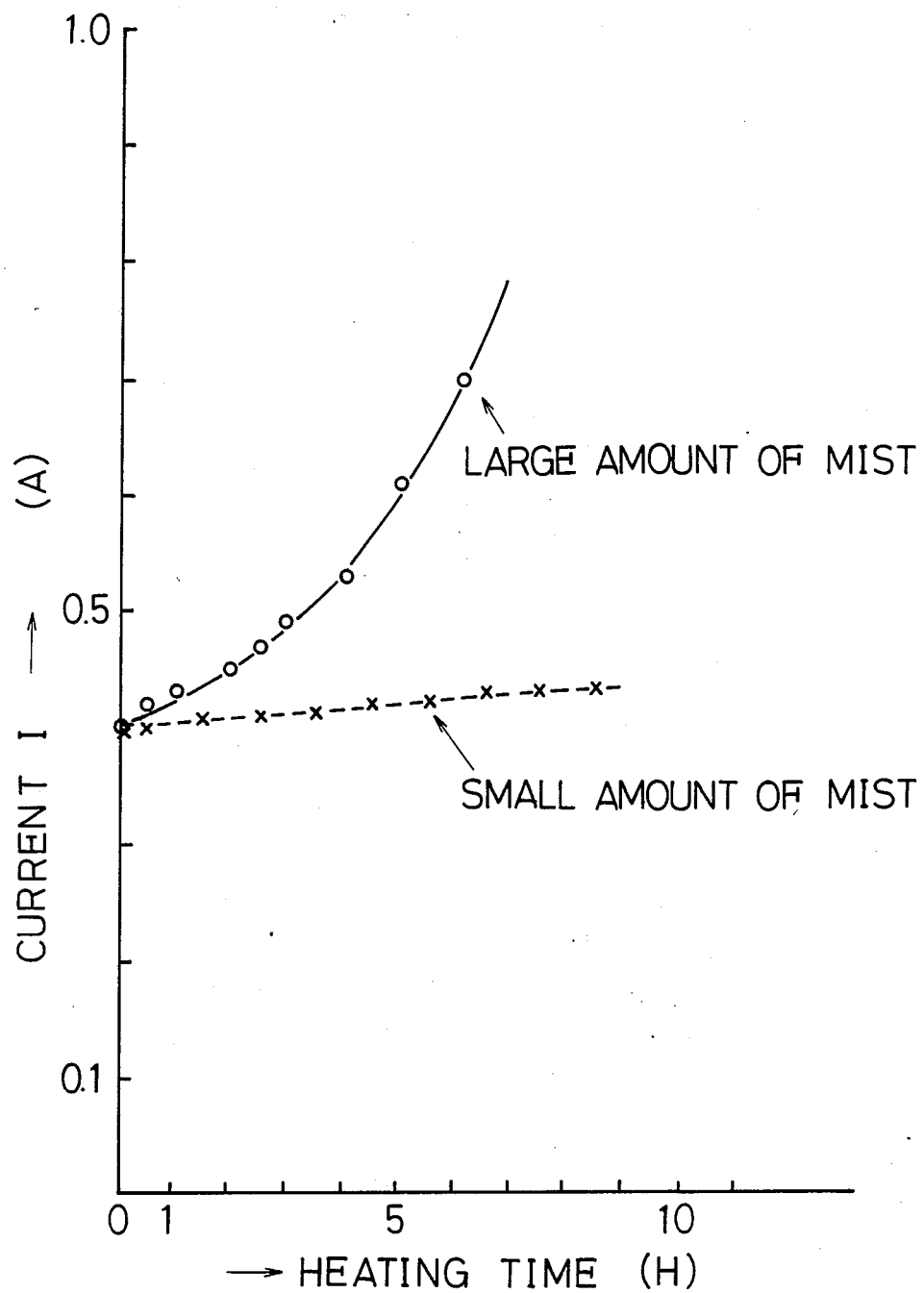
FIG. 3 is a graph showing the characteristics of the oil mist detector of said first embodiment.
Figure 4:
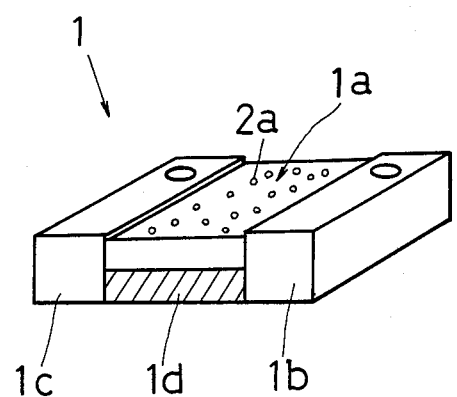
FIG. 4 is a schematic illustration showing a second embodiment of the oil mist detector according to this invention.

FIG. 3 shows a particular example of charactristics of oil mist detection by an oil mist sensor having about 5 W capacity with the construction shown in FIG. 4.

The abscissa represents time for heating a mist sensor in helium gas used for a compressor and the ordinate represents current for heating the mist sensor.

In this example are shown the cases of a small amount of several ten ppm oil mist and a large amount of several thousand ppm oil mist. As is apparent from FIG. 3, heating current ih increases in proportion to the heating time, i.e., integrated amount of the oil mist and further the larger the oil mist amount is, the larger the increase of the heating current i is. From FIG. 3, the current i immediately after the heating is found to be about 0.4 amps (A). Thus, this value corresponds to the heating current ih for the heating wire $1d$ described in FIG. 1 and on the basis of this ih, the leak current im due to the oil mist is increased. For example, in the time point of heating time 5 hours (H), $i \approx 0.7$ A. Thus, the leak current im due to the oil mist is i−ih, i.e., im=0.7−0.4=0.3 A.

This leak current im can be indicated as the oil mist amount by the indicating means 5 or the like shown in FIG. 1.

Next will be described another embodiment related to the oil mist sensor with reference to FIG. 4.

Parts displaying the same operational effect as the mist sensor 1 described in FIG. 2 are designated by the same symbols.

In FIG. 4, the mist sensor 1 is provided on the end faces of the coating $1a$ made of material having insulating and heating resisting properties like ceramic with a pair of terminal portions $1b$, $1c$, and the heating unit $1d$ like ceramic heater or film heater is provided on the back of the coating $1a$ together with a pair of terminal portions $1b$, $1c$ so as to supply current to the heating unit $1d$.

According to the mist sensor 1 thus constituted, when the coating $1a$ is heated by the heating unit $1d$, the oil mist 2 attached to the coating $1a$ is decomposed to provide the deposit $2a$. The amount of deposit $2a$ due to the oil mist can be detected as the leak current between the terminal portions $1b$, $1c$.

Since the mist sensor 1 thus constituted can be made extremely thin and compact, the oil mist can be detected by the heating unit having low heat capacity.

As above mentioned, in the oil mist sensor according to this invention, the oil mist attaching surface of the coating $1a$ in FIG. 2 and the coating $1a$ in FIG. 4 of the corresponding sensor 1 is made of ceramic material having porosity or rough particles. This efficiently attaches the mist to the surface for baking and deposition.

Also, while the sensor means 1 is circular cylindrical and planar in FIGS. 2 and 4, it may be of cylindrical or other any forms.

An important point of the oil mist sensor is that the oil mist is baked on the surface of the sensor means 1 and temperature is set to one at which the oil mist can be deposited.

It is found from some experiments that the optimum baking temperature of the oil mist in the sensor is 750°–900° C. Thus, the determination of the size and heat capacity of the mist sensor 1 will do if it sets the surface temperature of the mist sensor 1 within said range.

Further the sensor has the following large effect. That is, it can self-clean the deposit of oil mist baked on the surface of the sensor. While the process of the oil mist baked on the sensor 1 is from the baking of the surface of heater at 850° C. in oil mist helium gas to deposit of hydrocarbon, the deposit on the surface of sensor has the main component of carbon so that it can be burnt in air. That is, the process is as follow;

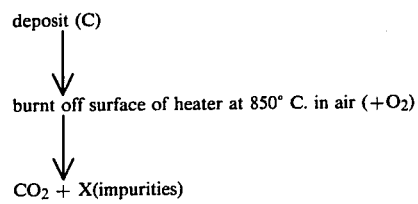

Thus the deposit on the surface of the sensor can be removed and cleaned.

As a result, this oil mist sensor has a large feature that when the oil mist sensor detects any abnormalities in the oil mist and the sensor means is operated in air after adjusting abnormal portions of the compressor, the deposit baked on the surface of the sensor is removably burnt by its own heating temperature to permit the reuse of the sensor very easily.

While the embodiment of the oil mist sensor applied to compressor according to this invention has been heretofore described, it can be of course applied to the oil mist detection in a low temperature compression refrigerating machine and compressor using non-inflammable gas like helium gas.

Further, the circumstances in which the surface temperature of sensor is maintained at 750°–900° C. in non-inflammable gas like helium will suffice for the atmosphere to which the oil mist sensor can be applied, and will be hardly affected by the pressure and temperature in the atmosphere.

Furthermore, the heater can be formed of one having 3–5 W of capacity and the mist sensor itself can have a very compact and simple construction so that it can be attached directly to the refrigerator, compression chamber for compressor or the like to play a large part in maintaining the performance of these machines.

What is claimed is:

1. An oil mist detector, comprising:
   a heating unit disposable in an inert gas having an oil mist therein, whereby said oil mist is deposited on said detector and decomposed by heat from said heating unit into a conductive carbon deposit,
   means for applying a voltage across said deposit; and
   detecting means for detecting an amount of current leaking through said deposit.

2. An oil mist detector according to claim 1, including:
   a coating of said heating unit, said coating having insulating and heat resisting properties;
   power source means for supplying current to said heating unit to heat said heating unit and for applying said voltage across said deposit;
   load means for detecting the current supplied by said power source; and
   an indicating means for indicating the current detected by said load means as an amount of said oil mist.

* * * * *